(12) United States Patent
Joseph Groenewegen et al.

(10) Patent No.: US 6,544,546 B1
(45) Date of Patent: *Apr. 8, 2003

(54) RING-SHAPED DEVICES

(75) Inventors: Rudolf Johannes Joseph Groenewegen, Heesch (NL); Antonius Paulus Sam, Heesch (NL); Herman Vromans, Oss (NL); Hendrik de Nijs, Oss (NL)

(73) Assignee: Akzo Nobel, N.V., Arnhem (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/981,881

(22) PCT Filed: Jul. 1, 1996

(86) PCT No.: PCT/EP96/02935

§ 371 (c)(1),
(2), (4) Date: Dec. 31, 1997

(87) PCT Pub. No.: WO97/02015

PCT Pub. Date: Jan. 23, 1997

(30) Foreign Application Priority Data

Jul. 4, 1995 (EP) .............................................. 95201818

(51) Int. Cl.$^7$ .................................................. A61F 6/08
(52) U.S. Cl. ........................................ 424/432; 514/843
(58) Field of Search ................................. 424/432, 425, 424/434, 435, 430; 128/830

(56) References Cited

U.S. PATENT DOCUMENTS

| | | | | |
|---|---|---|---|---|
| 4,188,951 A | * | 2/1980 | Higuchi et al. | |
| 4,237,885 A | | 12/1980 | Wong et al. | ................. 128/260 |
| 4,292,965 A | * | 10/1981 | Nash et al. | ................. 128/260 |
| 4,596,576 A | * | 6/1986 | De Nijs | ....................... 604/892 |

FOREIGN PATENT DOCUMENTS

| | | |
|---|---|---|
| EP | 050867 | 5/1982 |
| FR | 2 347-053 | 10/1975 |

* cited by examiner

Primary Examiner—Russell Travers
Assistant Examiner—Alysia Berman
(74) Attorney, Agent, or Firm—Allen C. Turner; William M. Blackstone

(57) ABSTRACT

A ring-shaped device for controlled release of hormonal compounds comprising a first compartment having a non-medicated core of ethylene-vinyl-acetate copolymer encircled by a steroid hormone loaded ethylene-vinyl-acetate copolymer middle layer and a non-medicated outer layer of ethylene-vinyl-acetate copolymer. The device also contains a second compartment having a core of ethylene-vinyl-acetate copolymer loaded with a steroid hormone and a non-medicated outer layer of ethylene-vinyl-acetate copolymer.

18 Claims, 1 Drawing Sheet

RING-SHAPED DEVICES

This application is a 371 of PCT/EP96/02935 filed Jul. 1, 1996.

The invention relates to ring-shaped devices and to a method of manufacture the same.

The invention relates in particular to ring-shaped vaginal devices, i.e. to vaginal rings.

Ring-shaped devices, and especially vaginal rings, are well known in the art. A two-layered one-compartment vaginal ring, for example, is disclosed in U.S. Pat. No. 4,237,885, in which a drug (progestational or estrogenic steroid) on a carrier is encircled by a polymeric tube, consisting of an ethylene-vinylacetate copolymer, both ends of which are joined together with a solid polymeric plug. Devices of this type, however, do not provide acceptable release patterns. Improvement was sought by using other shapes or other materials. A two-layered one-compartment vaginal ring made from silicone elastomer has been disclosed in EP 0,050,867, which ring comprises a silicone elastomer core loaded with active substance surrounded by a non-loaded silicone elastomer layer, which consists of two different compositions. Another improvement was claimed in U.S. Pat. No. 4,292,965, which disclosed a three-layered one-compartment ring. This ring comprises an inert silicone elastomer core encircled by a medicated silicone layer, and a non-medicated silicone outer layer. These above-mentioned one-compartment rings have the disadvantage that, when loaded with more than one active substance, release patterns of these substances can not be adjusted independently. Such devices usually show sub-optimum release patterns for the different substances, whereas it is generally preferred that all substances are released in a controlled rate and during a similar duration of time. As a consequence the release ratio of the active substances undergoes a change after a period of time.

In an attempt to solve these problems a two-compartment vaginal ring has been disclosed in U.S. Pat. No. 4,596,576. This device comprises two two-layered compartments, each containing another active substance. An advantage of this device is that the release ratio can be changed by changing the lengths of the compartments. To achieve a suitable ring with a constant release ratio, it is however necessary to join the ends of the compartments by using inert stoppers, which completely prevent mixing of the active ingredients. One of the disadvantages of this device is the expensive and difficult method to join the compartment ends to the stoppers, which method can hardly be automated.

Apart from unfavourable release patterns, changing release ratios, and burst effects (excessive release in the first few days), which are frequently occurring with the known vaginal rings, most vaginal rings are prepared from silicone elastomer, which material is nowadays considered as less safe.

It is an objective of the present invention to provide a safe ring-shaped device, with a good release pattern, preventing the disadvantages of the known vaginal rings, and which can be manufactured in a simple automated manner. Another objective of the invention is to provide a ring-shaped device which, after introduction thereof into the vagina, releases the steroid hormones within a short time, preferably within one to two days, to reach the desired plasma levels.

It has been found that a ring-shaped device comprising:
(a) a first compartment comprising a non-medicated core of ethylene-vinylacetate copolymer, encircled by a steroid hormone loaded ethylene-vinylacetate copolymer middle layer, and a non-medicated outer layer of ethylene-vinylacetate copolymer;
(b) a second compartment comprising a core of ethylene-vinylacetate copolymer loaded with a steroid hormone and a non-medicated outer layer of ethylene-vinylacetate copolymer; and
(c) optionally placebo segments of a thermoplastic material separating the first from the second compartment, fulfils these requirements.

The ring-shaped device according to the invention, is preferably a vaginal ring which can be used for hormone replacement therapy (HRT) or contraception.

The ethylene-vinylacetate copolymer can be any commercially available ethylene-vinylacetate copolymer, for instance as available under the trade names Elvax®, Evatane®, Lupolen V®, Movriton®, Ultrathene®, and Vestypar®.

The thermo-plastic material of the placebo segments can be any thermo-plastic material suitable for pharmaceutical use, such as polypropylene; low, linear low, or very low density polyethylene; ethylene-vinylacetate copolymer, and, preferably, high density polyethylene, such as commercially available Alathon®, Alkathene®, Baylon V®, Carlona®, Carlona P®, Dow PE®, Eltex®, Elvax®, Evatane®, Ferlene®, Fortilene®, Hi-fax®, Hostaflex®, Hostalen G®, Hostalen PP®, Lactene®, Lupolen®, Lupolen V®, Lyton®, Moplen®, Movriton®, Novatec®, Novolen®, Pro-fax®, Propathene®, Rigidex®, Stamylan®, Stamylan P®, Stamylex®, Teamex®, Tenite®, Trolen PP®, Typar®, Ultrathene®, VestolenP®, Vestypar®, and Vestolen A®.

Particularly good release patterns are obtained when the ethylene-vinylacetate copolymer middle layer of the first compartment is saturated with the progestogen and the ethylene-vinylacetate copolymer core of the second compartment is loaded with a just saturated, and most preferably with a sub-saturated mixture of the progestogen and the estrogen.

Preferred devices for contraceptive use have a first compartment wherein the steroid hormone is a progestogen and a second compartment wherein the steroid hormone is a mixture of a progestogen and an estrogen. Devices especially intended for HRT may advantageously have a first compartment loaded with a mixture of a progestogen and an estrogen and a second compartment loaded with a progestogen. The progestogens of the first and the second compartment may be the same or may be different.

Typically the ethylene-vinylacetate copolymer middle layer of the first compartment comprises the progestogen (or the mixture of the progestogen and the estrogen) in crystalline form.

The lengths of the compartments of the ring-shaped device are chosen to give the required performance. Ratios of the lengths of the first and second compartment are contemplated to be between 30:1 and 1:30, but usually are between 15:1 and 1:1, and preferably are about 2:1. The lengths of the placebo segments are long enough to prevent excessive mixing of the progestogen of the first compartment with the progestogen and/or estrogen of the second compartment. This is usually attained by applying placebo segments of a length between 0.5 and 70 mm. The necessary length depends on the nature of the thermo-plastic material and its capacity to prevent permeation of the active materials. Most ideally the placebo segment completely prevents mixing, since mixing disturbs the release pattern. In practice, however, some mixing, in particular after a longer period of time, occurs due to diffusion of the active ingredients through the placebo segment from one to the other compartment. Such mixing would ultimately lead to the same load of estrogen in both compartments, which of course is unwanted when the loads are meant to be different. Some minor mixing however, is not completely to be prevented and is allowed to the point that the mixing influences the release of the active ingredients in such a manner that plasma levels of active ingredients get outside the required values. In practice less than 10% mixing, and preferably less than 5% mixing one month after insertion of the device, is acceptable. Usually a length of the placebo segments being preferably about at least half of the length of the second compartment is sufficient to prevent excessive mixing.

The ring-shaped device can be manufactured in any size as required. In practice, however an outer ring diameter of about 53.5 mm, a cross sectional diameter of about 3.5 mm, a length of the first compartment of about 100 to 110 mm, a length of the second compartment of about 10 to 40 mm, and a length of each of the two placebo segments of about 5 to 20 mm, has been proven to be very suitable for all purposes. If no placebo segments are used the length of the first compartment is about 110 and the length of the second compartment is preferably 42–52 mm.

The progestogen can be any suitable progestogen, such as desogestrel, etonogestrel (3-ketodesogestrel), levonorgestrel, norgestrel, gestodene, and other compounds with similar progestogenic activity. Preferably the progestogen is etonogestrel. The estrogen can be any suitable estrogen, such as estradiol, estriol, mestranol, and ethinyl estradiol. For contraceptive use ethinyl estradiol is preferred, whereas for HRT estradiol is the preferred estrogen.

Using the most preferred ring-shaped device of the invention, the ethylene-vinylacetate copolymer layer of the first compartment is loaded with 5–60% w/w, and preferably with about 15% w/w of etonogestrel, and the ethylene-vinylacetate copolymer core of the second compartment is loaded with 0.05–3% w/w, and preferably about 0.25–0.5% w/w of etonogestrel and 0.05–5% w/w, and preferably about 0.75–1.5% w/w of ethinyl estradiol.

The preferred vaginal ring releases at least 90 µg/day of etonogestrel and 10 µg/day of ethinyl estradiol, with an upper limit of 450 µg/day and 100 µg/day respectively during Day 1–3, and 150 µg/day and 20 µg/day respectively during Day 4–21.

The ring-shaped devices can be prepared in any suitable manner for the manufacture of vaginal rings. A preferred method of manufacture of the ring-shaped device comprises co-extrusion of the core and the layer(s), medicated or non-medicated as required, of each of the first and second compartments to render a fibre with a medicated middle or core layer, respectively. These fibres are cut into pieces of the required lengths, and the pieces are assembled to the ring-shaped device in a mould kept at about 40° C., by injection moulding with high density polyethylene of about 230° C. The rings are thereafter packed in the usual manner.

Another method of manufacture is a welding technique, for instance the hot-gas welding technique, which is especially suitable when no placebo segments are used. This technique is well known in the art. Basically the hot-gas technique is performed in an apparatus consisting of two moulds which are used to clamp the fibre ends and hold them in line to each other. One mould is static and the other is movable. A movable stop is used to assure that the fibre ends are only sticking out of the mould by about 0.5 mm. The apparatus further comprises a capillary which is used to remove residual polymer. The capillary consists of two identical halves, one of which is mounted on the upper part of a mould and the other is mounted on the lower part of the mould. A hot-air gun is used to melt the fibre ends.

In another embodiment the two ethylene-vinylacetate copolymer fibres, loaded with either etonogestrel or a mixture of etonogestrel and ethinyl estradiol, are melt co-extruded together with the skin-core ethylene-vinylacetate copolymer to render a skin-core fibre. These skin-core fibres are cut into pieces of the required length and assembled to a ring in a mould with two suitable pieces injection moulded high density polyethylene and injection moulded at 230° C., with a mould temperature of 40° C. The rings are thereafter sterilised and packed in the usual manner, for instance packed in a sachet consisting of a PET (12 µm)/aluminium (9 µm)/LDPE (40 µm) laminate.

The invention is illustrated by the Figures.

Figure 1:
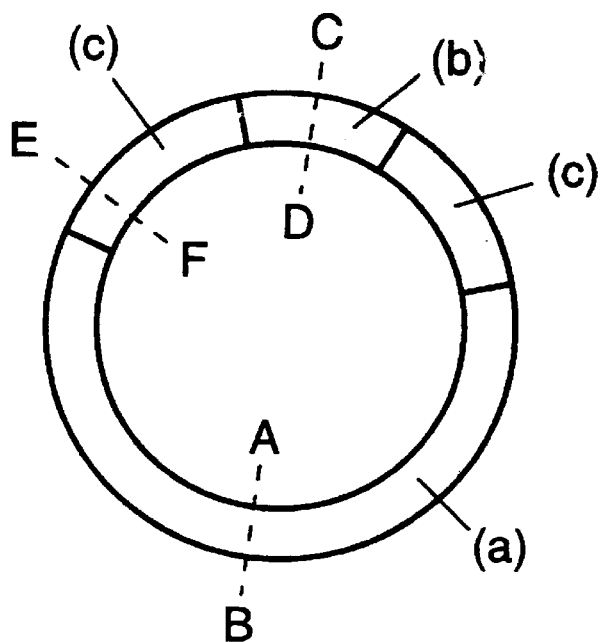
FIG. 1 shows schematically an embodiment of a vaginal ring according to this invention, containing the first compartment (a), the second compartment (b) and two placebo segments (c).
Figure 2:
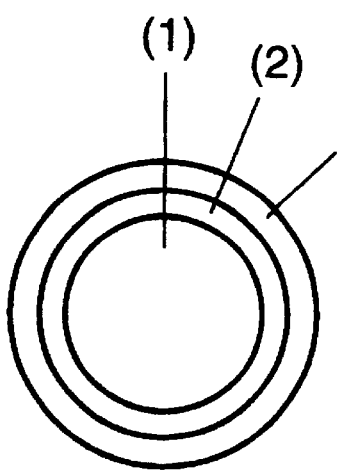
FIG. 2 shows a cross-section along the line A–B of the first compartment.
Figure 3:
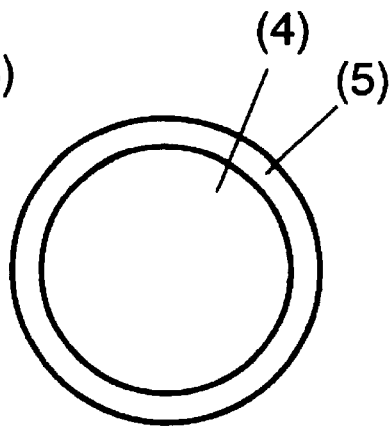
FIG. 3 shows a cross-section along the line C–D of the second compartment.
Figure 4:
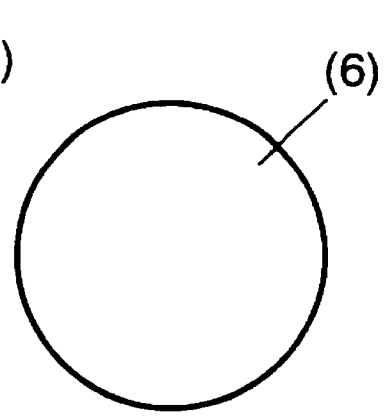
FIG. 4 shows a cross-section along the line E–F of a placebo segment.

In these drawings an embodiment of the invention is disclosed. The device is made of three compartments (a), (b), and (c), the first two of which comprise an ethylene-vinylacetate copolymer core (1) and (4) respectively, and the latter is an thermo-plastic placebo segment. In the first compartment (FIG. 2) the core (1) is non-medicated, and it further comprises an ethylene-vinylacetate copolymer middle layer (2) loaded with active ingredient, and an ethylene-vinylacetate copolymer outer layer (3) which is non-medicated. In FIG. 3 the core (4) is loaded with active ingredient, which core is surrounded by an ethylene-vinylacetate copolymer outer layer (5) which is non-medicated. The placebo segments (FIG. 4) preferably consist of one layer of non-medicated thermoplastic material (6).

The invention is further illustrated by the following examples.

EXAMPLE 1

A vaginal ring is composed from two steroid loaded compartments and two placebo segments, having the following composition and dimensions (see Figures):

First Compartment (FIG. 2)
  a three-layered fibre comprising:
    core (1): Evatane® 1040 VN4; diameter 2.96 mm; middle layer (2) loaded with 15% w/w of etonogestrel in Evatane® 28–25; thickness 75 µm, extruded at 105° C.; outer layer (3): Evatane® 1040 VN4; thickness 195 µm.
  The steroid loaded mixture and Evatane® 1040 VN4 are co-extruded at 120° C. to form a trilayer fibre.

Second Compartment (FIG. 3)
  a two-layered fibre comprising:
    core (4): Evatane® 28–25 loaded with 0.5% w/w of etonogestrel and 1.5% w/w of ethinyl estradiol (EE); diameter 3.35 mm, extruded at 105° C.; outer layer (5): Evatane® 1020 VN3; thickness 75 µm.
  The steroid loaded mixture and Evatane® 1020 VN3 are co-extruded at 110° C. to form a skin-core fibre.

Placebo Segments (FIG. 4)
  two placebo segments of 16 mm length each, comprising Stamylex® 9119 (6); diameter 3.5 mm.

The trilayer fibre is cut into fibre pieces of 110 mm and the skin-core fibre is cut into fibre pieces of 15 mm. One small and one large fibre piece are joined together to a ring-shaped device by injection moulding of the two placebo segments (HDPE) at 230° C., with a mould temperature of 40° C.

EXAMPLE 2

According to the procedure of Example 1, ring-shaped devices were prepared comprising compartments having the following content:

First Compartment skin/core: Evatane® 1040 VN4; middle layer: Evatane® 28–25 loaded with etonogestrel; outer diameter 3.5 mm.

| Medicated layer load (% w/w) | skin thickness (µm) | medicated layer thickness (µm) | extrusion temp. (° C.) |
|---|---|---|---|
| 10 | 230 | 75 | 120 |
| 15 | 195 | 75 | 120 |
| 15 | 230 | 75 | 120 |
| 15 | 265 | 75 | 120 |
| 15 | 230 | 75 | 145 |
| 15 | 175 | 75 | 120 |
| 15 | 195 | 65 | 120 |
| 15 | 195 | 85 | 120 |

Second Compartment core: Evatane® 28–25 loaded with etonogestrel and ethinyl estradiol (EE); outer layer: Evatane® 1020 VN3 or Evatane® 1040 VN4; outer diameter 3.5 mm.

| medicated layer load etonogestrel (% w/w) | medicated layer load EE (% w/w) | skin thickness (µm) | extrusion temp. (° C.) |
|---|---|---|---|
| skin material: Evatane ® 1020 VN3 | | | |
| 0.5 | 1.5 | 65 | 105 |
| 0.5 | 1.5 | 80 | 105 |
| 0.8 | 1.5 | 50 | 105 |
| 0.8 | 1.5 | 65 | 105 |
| 0.8 | 1.5 | 80 | 105 |
| 0.5 | 1.5 | 75 | 105 |
| 0.5 | 1.5 | 75 | 103 |
| 0.5 | 1.5 | 75 | 115 |
| 0.45 | 1.5 | 75 | 110 |
| 0.5 | 1.5 | 75 | 110 |
| 0.55 | 1.5 | 75 | 110 |
| 0.5 | 1.35 | 75 | 110 |
| 0.5 | 1.65 | 75 | 110 |
| 0.25 | 0.75 | 85 | 110 |
| skin material: Evatane ® 1040 VN4 | | | |
| 0.37 | 1.1 | 345 | 120 |
| 0.37 | 1.1 | 380 | 110 |
| 0.37 | 1.1 | 425 | 110 |

Placebo Segments two placebo segments of 16 mm length each, comprising Stamylex® 9119.

EXAMPLE 3

The following first compartments containing etonogestrel were prepared. Medicated layer material is Evatane® 28–25; outer diameter is 3.5 mm.

| entry | skin/core Evatane ® | medicated layer load etonogestrel % w/w | skin thickness µm | medicated layer thickness µm | extrusion temp. ° C. |
|---|---|---|---|---|---|
| 1 | 1040 VN4 | 10 | 230 | 75 | 120 |
| 2 | 1040 VN4 | 15 | 195 | 75 | 120 |
| 3 | 1040 VN4 | 15 | 230 | 75 | 120 |
| 4 | 1040 VN4 | 15 | 265 | 75 | 120 |
| 5 | 1040 VN4 | 15 | 230 | 75 | 145 |
| 6 | 1040 VN4 | 15 | 195 | 65 | 120 |
| 7 | 1040 VN4 | 15 | 195 | 85 | 120 |

The following second compartments containing etonogestrel and ethinyl estradiol (EE) were prepared. Medicated layer material is Evatane® 28–25; outer diameter is 3.5 mm:

| entry | skin Evatane ® | medicated layer load | | skin thickness µm | extrusion temp. ° C. |
|---|---|---|---|---|---|
| | | etonogestrel % w/w | EE % w/w | | |
| 8 | 1020 VN3 | 0.5 | 1.5 | 65 | 105 |
| 9 | 1020 VN3 | 0.5 | 1.5 | 80 | 105 |
| 10 | 1020 VN3 | 0.8 | 1.5 | 50 | 105 |
| 11 | 1020 VN3 | 0.8 | 1.5 | 65 | 105 |
| 12 | 1020 VN3 | 0.8 | 1.5 | 80 | 105 |
| 13 | 1020 VN3 | 0.5 | 1.5 | 75 | 105 |
| 14 | 1020 VN3 | 0.5 | 1.5 | 75 | 103 |
| 15 | 1020 VN3 | 0.5 | 1.5 | 75 | 115 |
| 16 | 1020 VN3 | 0.45 | 1.5 | 65 | 110 |
| 17 | 1020 VN3 | 0.5 | 1.5 | 75 | 110 |
| 18 | 1020 VN3 | 0.55 | 1.5 | 75 | 110 |
| 19 | 1020 VN3 | 0.5 | 1.35 | 75 | 110 |
| 20 | 1020 VN3 | 0.5 | 1.65 | 75 | 110 |
| 21 | 1020 VN3 | 0.25 | 0.75 | 75 | 120 |
| 22 | 1040 VN4 | 0.37 | 1.1 | 345 | 120 |
| 23 | 1040 VN4 | 0.37 | 1.1 | 380 | 110 |
| 24 | 1040 VN4 | 0.37 | 1.1 | 425 | 110 |

The following vaginal rings were prepared according to the method of Example 1:

(a) first compartment of material of entry 6 (110 mm); second compartment of material of entry 9 (15 mm); placebo segments of Stamylex® 9119 (16 mm).

(b) first compartment of material of entry 7 (110 mm); second compartment of material of entry 13 (16 mm); placebo segments of Stamylex® 9119 (16 mm).

(c) first compartment of material of entry 7 (110 mm); second compartment of material of entry 13 (15 mm); placebo segments of Stamylex® 9119 (16 mm).

(d) first compartment of material of entry 6 (110 mm); second compartment of material of entry 21 (20 mm); placebo segments of Stamylex® 9119 (15.5 mm).

(e) first compartment of material of entry 6 (110 mm); second compartment of material of entry 21 (30 mm); placebo segments of Stamylex® 9119 (8.5 mm).

(f) first compartment of material of entry 7 (110 mm); second compartment of material of entry 13 (17 mm); placebo segments of Stamylex® 9119 (13 mm).

(g) first compartment of material of entry 6 (110 mm); second compartment of material of entry 22 (20 mm); placebo segments of Stamylex® 9119 (13.5 mm).

(h) first compartment of material of entry 7 (110 mm); second compartment of material of entry 22 (21 mm); placebo segments of Stamylex® 9119 (13 mm).

(i) first compartment of material of entry 6 (110 mm); second compartment of material of entry 22 (24 mm); placebo segments of Stamylex® 9119 (8.5 mm).

(j) first compartment of material of entry 6 (110 mm); second compartment of material of entry 23 (21 mm); placebo segments of Stamylex® 9119 (12 mm).

(k) first compartment of material of entry 6 (110 mm); second compartment of material of entry 24 (21 mm); placebo segments of Stamylex® 9119 (12 mm).

EXAMPLE 4

A vaginal ring is composed from two steroid loaded compartments having the following composition and dimensions (see Figures):
First Compartment (FIG. 2)
a three-layered fibre comprising:
core (1): Evatane® 1040 VN4; diameter 2.96 mm; middle layer (2) loaded with 15% w/w of etonogestrel in Evatane® 28–25; thickness 75 μm, extruded at 105° C.; outer layer (3): Evatane® 1040 VN4; thickness 195 μm.

The steroid loaded mixture and Evatane® 1040 VN4 are co-extruded at 120° C. to form a trilayer fibre.
Second Compartment (FIG. 3)
a two-layered fibre comprising:
core (4): Evatane® 28–25 loaded with 0.25% w/w of etonogestrel and 0.75% w/w of ethinyl estradiol (EE); diameter 3.35 mm, extruded at 105° C., outer layer (5): Evatane® 1020 VN3; thickness 145 μm.

The steroid loaded mixture and Evatane® 1020 VN3 are co-extruded at 110° C. to form a skin-core fibre.

The trilayer fibre is cut into fibre pieces of 110 mm and the skin-core fibre is cut into fibre pieces of 47 mm. One small and one large fibre piece are joined together to a ring-shaped device by hot-gas welding technique.

EXAMPLE 5

The following first compartments containing etonogestrel were prepared. The medicated layer material is Evatane 28–25; the skin/core material is Evatane 1040 VN4 (outer diameter is 3.5 mm).

| Entry | Medicated layer load (% w/w) | Skin thickness (μm) | Medicated layer thickness (μm) | Extrusion temp. (° C.) |
|---|---|---|---|---|
| 25 | 15 | 175 | 75 | 120 |
| 26 | 15 | 140 | 75 | 120 |
| 27 | 15 | 220 | 75 | 120 |

The following second compartments containing etonogestrel and ethinyl estradiol (EE) were prepared. The medicated layer material is Evatane 28–25; the skin material is Evatane 1020 VN3 (outer diameter is 3.5 mm).

| | medicated layer load | | | |
|---|---|---|---|---|
| Entry | Etonogestrel (% w/w) | EE (% w/w) | skin thickness (μm) | extrusion temp. (° C.) |
| 28 | 0.25 | 0.75 | 85 | 110 |
| 29 | 0.25 | 0.75 | 125 | 110 |
| 30 | 0.25 | 0.75 | 145 | 110 |
| 31 | 0.30 | 0.90 | 175 | 110 |
| 32 | 0.20 | 0.60 | 115 | 110 |
| 33 | 0.15 | 0.45 | 145 | 110 |

The following vaginal rings were prepared according to the method of example 4:

a) First compartment of material of entry 2 (110 mm) second compartment of material of entry 31 (47 mm)

b) First compartment of material of entry 2 (110 mm) second compartment of material of entry 32 (47 mm)

c) First compartment of material of entry 25 (100 mm) second compartment of material of entry 30 (50 mm)

d) First compartment of material of entry 6 (110 mm) second compartment of material of entry 30 (47 mm)

e) First compartment of material of entry 7 (110 mm) second compartment of material of entry 29 (40 mm)

f) First compartment of material of entry 26 (80 mm) second compartment of material of entry 33 (75 mm)

g) First compartment of material of entry 27 (125 mm) second compartment of material of entry 28 (30 mm)

What is claimed is:

1. A ring-shaped device comprising:
   (a) a first compartment comprising a non-medicated core of ethylene-vinylacetate copolymer, encircled by steroid hormone loaded ethylene-vinylacetate copolymer middle layer, and a non-medicated outer layer of ethylene-vinylacetate copolymer;
   (b) a second compartment comprising a core of ethylene-vinylacetate copolymer loaded with a steroid hormone and a non-medicated outer layer of ethylene-vinylacetate copolymer; and
   wherein the ethylene-vinylacetate copolymer middle layer of the first compartment is saturated with the steroid hormone and comprises steroid hormone is crystalline form, said first compartment having been manufactured by co-extruding the core, the middle layer and the outer layer, wherein during co-extrusion the middle layer is saturated with steroid hormone and comprises steroid hormone in crystalline form, and wherein said ring-shaped device possesses an unexpectedly uniform steroid hormone release.

2. The ring-shaped device of claim 1, wherein the steroid hormone of the middle layer of the first compartment is a progestogen, and the ethylene-vinylacetate copolymer core of the second compartment is loaded with a mixture of a progestogen and an estrogen.

3. The ring-shaped device of claim 2, wherein the ethylene-vinylacetate copolymer middle layer of the first compartment is saturated with the progestogen, and the ethylene-vinylacetate copolymer core of the second compartment is loaded with a sub-saturated mixture of the progestogen and the estrogen.

4. The ring-shaped device of claim 2, wherein the progestogen is etonogestrel and the estrogen is ethinyl estradiol.

5. The ring-shaped device of claim 4, wherein the middle ethylene-vinylacetate copolymer layer of the first compartment is loaded with about 15% w/w of etonogestrel, and the ethylene-vinylacetate copolymer core of the second compartment is loaded with about 0.25 to 0.5% w/w of etonogestrel and about 0.75 to 1.5% w/w of ethinyl estradiol.

6. The ring-shaped device of claim 5, wherein at least 90 µg/day of etonogestrel and 10 µg/day of ethinyl estradiol release from the ring-shaped device.

7. The ring-shaped device of claim 6, wherein, at most, 450 µg/day of etonogestrel and 100 µg/day of ethinyl estradiol release from the ring-shaped device during days 1–3.

8. The ring-shaped device of claim 7, wherein, at most, of 150 µg/day of etonogestrel and 20 µg/day of ethinyl estradiol release from the ring-shaped device during days 4–21.

9. The ring-shaped device of claim 1, wherein the lengths of the first and second compartment have a ratio of between 15:1 and 1:1.

10. The ring shaped device of claim 9, wherein the ratio is about 2:1.

11. A method of manufacture of the ring-shaped device of claim 1, comprising welding the first compartment to the second compartment.

12. The ring-shaped device of claim 1, further comprising placebo segments of a thermo-plastic material separating said first compartment from said second compartment.

13. The ring-shaped device of claim 12, wherein the lengths of the placebo segments are of sufficient length to prevent substantial mixing of the steroid hormone of the first compartment with the steroid hormone of the second compartment.

14. The ring-shaped device of claim 13, wherein each placebo segment is approximately at least half of the length of the second compartment.

15. The ring-shaped device of claim 12, wherein the ring diameter is about 53.5 mm, the cross sectional diameter is about 3.5 mm, the length of the first compartment is about 100 to 110 mm, the length of the second compartment is about 10–40 mm, and each of the two placebo segments has a length of about 5 to 20 mm.

16. The ring-shaped device of claim 12, wherein the thermo-plastic material of the placebo segments is high density polyethylene.

17. A method of manufacture of the ring-shaped device of claim 12, comprising co-extruding the core and the layers of the first and second compartments into a fibre, after which pieces of each fibre are assembled to the ring-shaped device by melting the pieces to the thermo-plastic material of the placebo segments in a mold.

18. The ring-shaped device of claim 1, wherein the ring diameter is about 53.5 mm, the cross sectional diameter is about 3.5 mm, the length of the first compartment is about 100 to 110 mm and the length of the second compartment is about 42 to 52 mm.

* * * * *